United States Patent [19]
Theiss et al.

[11] Patent Number: 6,033,421
[45] Date of Patent: Mar. 7, 2000

[54] TATTOO MACHINE

[75] Inventors: Scott Marsh Theiss, P.O. Box 636, Lake Lure, N.C. 28746; Pasco Forsyth Parker, Rte. 4 Box 538-B, Moneta, Va. 24121; Michael Maurice Banks, Box 414, Lake Lure, N.C. 28746; Marty Law Banks, 4569 Shelby Dr., Dalton, Ga. 30721

[73] Assignees: Scott Marsh Theiss, Lake Lure, N.C.; Pasco Forsyth Parker, Moneta, Va.; Michael Maurice Banks, Lake Lure, N.C.; Marty Law Banks, Dalton, Ga.

[21] Appl. No.: 08/893,382

[22] Filed: Jul. 11, 1997

[51] Int. Cl.⁷ .................................................. A61B 17/34
[52] U.S. Cl. ............................................................ 606/186
[58] Field of Search ..................................... 606/185, 186

[56] References Cited

U.S. PATENT DOCUMENTS

| | | |
|---|---|---|
| 464,801 | 12/1891 | O'Rilly . |
| 3,509,786 | 5/1970 | Bottner ...................................... 81/9.22 |
| 4,204,438 | 5/1980 | Binaris et al. ............................ 81/9.22 |
| 4,719,825 | 1/1988 | LaHaye et al. ........................... 81/9.22 |
| 4,796,624 | 1/1989 | Trott et al. ................................ 128/316 |
| 4,914,988 | 4/1990 | Chang ....................................... 81/9.22 |
| 5,165,488 | 11/1992 | Liu ............................................ 173/49 |
| 5,279,552 | 1/1994 | Magnet ..................................... 604/47 |
| 5,472,449 | 12/1995 | Chou ........................................ 606/186 |

FOREIGN PATENT DOCUMENTS 1 587 519   4/1981   United Kingdom .

*Primary Examiner*—Michael Buiz
*Assistant Examiner*—Vy Q. Bui
*Attorney, Agent, or Firm*—Rhodes & Mason PLLC

[57] ABSTRACT

A handheld tattoo machine with a low vibration drive unit and an offset, removable driven grip tube. The drive unit includes a rotatable drive shaft; a cam attached to the distal end of the shaft, the cam having a cam face at an angle to the longitudinal axis of the drive shaft; and a drive housing enclosing the drive shaft and cam. The drive housing includes a driven grip tube receiving bore having a longitudinal axis parallel to and offset from the longitudinal axis of the drive housing to facilitate ease of use by the operator. The removable driven grip tube includes a reciprocal needle bar having a cam follower at a proximal end and a needle attachment surface at a distal end.

24 Claims, 2 Drawing Sheets

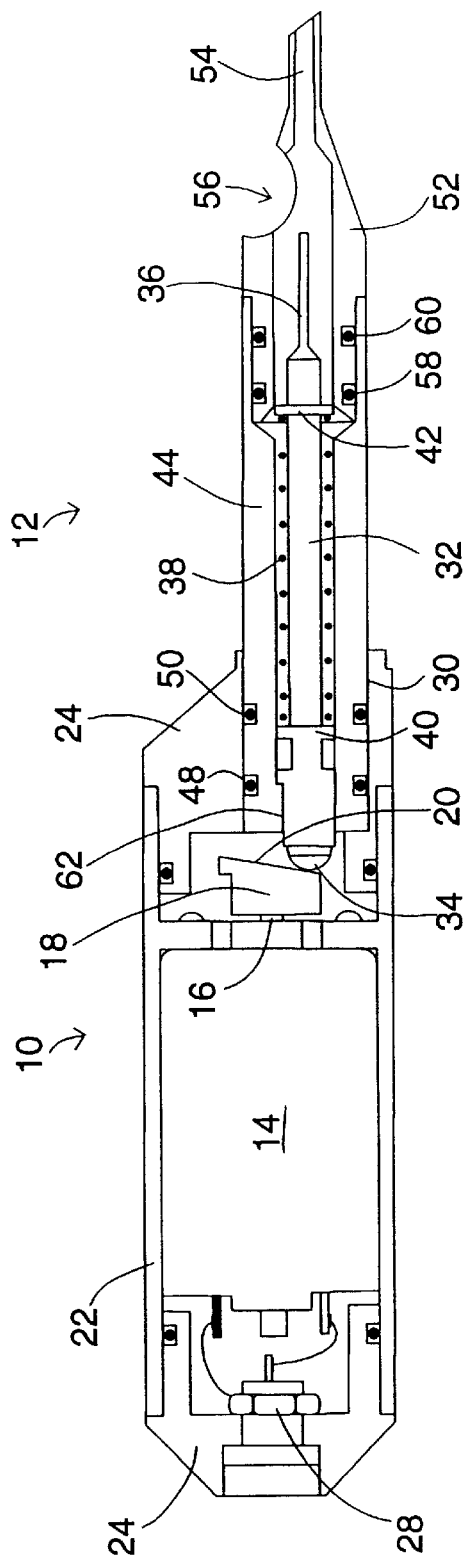
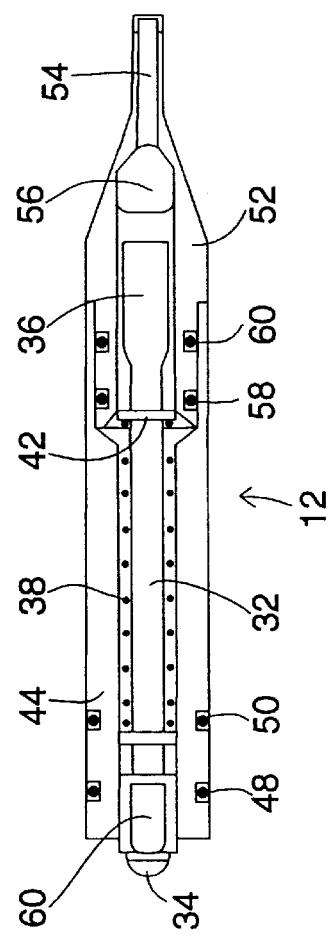

TATTOO MACHINE

BACKGROUND OF THE INVENTION

(1) Field of the Invention

The present invention relates generally to tattooing and, more particularly, to an improved tattoo machine for introducing a pigment beneath the skin to produce a tattoo or other design.

(2) Description of the Prior Art

Tattoos are applied by perforating the skin of a subject in a predetermined pattern with a needle and introducing one or more colored pigments into the perforations. Modern tattooing is performed using a tattoo instrument or tattoo machine comprised of needle holder to hold the tattooing needle, and an electric motor or other means, e.g., a solenoid, to rapidly reciprocate the needle.

The needle can be periodically dipped in the pigment, or the needle can reciprocate in contact with a reservoir of pigment to coat the pigment onto the needle. The needle holder is normally enclosed within a housing that also serves as a handgrip for the operator.

The prior art describes various tattoo machines based upon different arrangements of these elements. Designs proposed to date, however, have one or more limitations. Many of the designs are bulky, heavy or unbalanced, making it difficult for the operator to hold the tattoo machine steady during use, particularly when larger or complex designs are to be made. Other tattoo machines vibrate excessively during use, adversely affecting the ability of the operator to produce a detailed design. Finally, cleaning of the tattoo machine components after use, which is critical because of the presence of blood during tattooing, can be difficult and unreliable with prior art designs.

In preparation for tattooing, the operator attaches a needle to a needle holder. If more than one color of pigment is to be used during the tattooing process, the operator will prepare a plurality of needle carrying needle holders. Separate tattooing instruments can be used for each needle. Preferably, however, a single tattoo machine is used for all of the needles, with the needles being changed in the tattoo machine during the tattooing. Replacement of the needle holder in prior art tattoo machines is difficult, and requires an inordinate amount of time, reducing the operator's profit and extending the subject's discomfort.

Thus, there remains a need for a new and improved tattoo machine that is compact and easily held while, at the same time, does not vibrate excessively during use. There is a further need for a tattoo machine in which the needle holder can be quickly and easily replaced during use, and which can be quickly and easily cleaned after use.

SUMMARY OF THE INVENTION

The present invention is directed to an improved tattoo machine. The tattoo machine described herein is formed of a drive unit to which replaceable needle containing, driven grip tubes can be quickly attached. The configuration of the tattoo machine is such that the axis of the drive unit and the axis of the driven grip tube are eccentrically offset along parallel, spaced pathways, so that the relatively bulky drive unit is positioned to rest above the operator's hand, while the operator grips the relatively small diameter housing of the driven grip tube.

In the preferred embodiment, the tattoo machine of the present invention is comprised of a low vibration drive unit comprised of a drive shaft with an attached cam. The cam has a cam face toward the distal end of the tattoo machine. An electric motor is used to impart rotary motion to the shaft during use. The shaft may form a part of the electric motor, or can be connected to the motor by means of an intermediate flexible drive shaft.

The drive unit further includes a housing to enclose the shaft and cam, and the motor, if present. In the preferred embodiment, the housing is generally comprised of a tubular section with a central bore. An adapter cap containing a receiving bore for receiving the driven grip tube is fitted to the distal or back end of the tubular section, and a detachable end cap is fitted to the proximal or front end of the tubular section. The axis of the driven grip tube receiving bore is parallel to the axis of the drive shaft, but offset or eccentric thereto, so that the driven grip tube receiver axis intersects the cam face between its center and edge.

The driven grip tube is designed to be easily insertable into the receiving bore of the drive unit housing to position the needle bar for engagement by the cam, thus permitting the ready substitution of different needles during use of the device, and is comprised of a needle bar within a housing that also serves as a hand grip. The needle bar includes a cam follower at its proximal end and a needle connector at its distal end. The cam follower is preferably rotatable to reduce friction, and may be in the form of a ball bearing fitted into a recess in the proximal end of the needle bar, a Teflon® tip or an ejection molded, wear-resistant plastic.

The needle connector may be or different configurations, depending upon the type of needle used, and the manner of attachment. For example, the needle connector may be a flat plate to which the needle is soldered. A spring is positioned around the needle bar to urge the needle bar toward the cam in the drive housing, and thus maintain contact between the cam face and cam follower. A washer or retainer is positioned around the needle bar at the distal end of the spring to hold the spring in place.

In the preferred embodiment, the driven grip tube housing is comprised of an elongated grip section having a needle bar receiving bore extending between its proximal and distal ends, and a tip section attachable to the terminal end of the elongated section. The cross-section of the grip section at the proximal end corresponds to the cross-section of the housing receiving bore so that the proximal end of the grip section will fit snugly into the bore.

The tip section includes an axial bore axially aligned with the needle bar receiving bore. The tip bore terminates in a needle exit opening that is of reduced diameter relative to the needle bar bore. The tip section also includes a pigment receiving opening or reservoir for introducing pigment into the interior of the tip section.

To prepare the tattoo machine for use, a needle is first attached to the needle connector. The needle bar is then inserted into the bore of the elongated grip section of the needle bar housing so that the cam follower projects from the proximal end of the bore, and the tip section of the needle bar housing is fitted onto the distal end of the needle bar housing. Contact of the spring retainer with the tip section urges the spring and needle bar to the proximal end of the needle bar housing.

The proximal end of the assembled driven grip tube is then inserted into the driven grip tube receiving bore of the drive unit housing, so that the cam follower engages the cam face. O-rings around the proximal ends of the tip section and the elongated section provide snug fits to reduce vibration and prevent the entry of liquids into the tattoo machine interior.

In operation, the drive shaft and attached cam are rotated at a high speed, e.g., up to about 10,000 rpm. As the cam turns, the cam follower rides along the face of the cam to push the needle bar to the distal end of the tattoo machine at least once per drive shaft rotation. The spring then forces the needle bar back toward the cam to hold the cam follower in engagement with the cam face.

When a different needle is required, the operator simply removes the driven grip tube from the receiving bore of the drive unit housing, and inserts a new driven grip tube with the other needle. Thus, changing of needles is quick and easy. In addition, due to the construction of the tattoo machine, the operator can grip the tattoo machine around the elongated grip tube needle bar housing, instead of around the bulky drive shaft housing. In addition, parallel, offset alignment of the drive shaft and grip tube axes produces a more easily held device.

Accordingly, one aspect of the present invention is to provide a handheld tattoo machine. The apparatus includes: (a) a driven grip tube including a reciprocal needle bar; and (b) a drive housing for receiving and driving the driven grip tube, the drive housing having a longitudinal axis parallel to and offset from the longitudinal axis of the grip tube to facilitate ease of operation of the tattoo machine.

Another aspect of the present invention is to provide a driven grip tube for a needle bar for attachment to the drive unit of a tattoo machine, the drive unit including a rotatable shaft with a first longitudinal axis, a cam rotatable by the shaft, the cam having a cam face at an angle to the longitudinal axis of the shaft, and a driven grip tube receiving bore. The driven grip tube includes: (a) a elongated cylindrical housing; and (b) a longitudinally reciprocal needle bar received within the housing having a cam follower at one end for engagement with the cam face and a needle attachment surface at an opposed end.

Still another aspect of the present invention is to provide a handheld tattoo machine. The apparatus includes: (a) a driven grip tube including: (i) a elongated cylindrical housing; and (ii) a longitudinally reciprocal needle bar received within the housing having a cam follower at one end and a needle attachment surface at an opposed end; and (b) a drive housing for receiving and driving the driven grip tube, the drive housing having a longitudinal axis parallel to and offset from the longitudinal axis of the grip tube to facilitate ease of operation of the tattoo machine, wherein the drive housing further includes a drive unit including a rotatable drive shaft and a cam attached to the distal end of the shaft, the cam having a cam face at an angle to the longitudinal axis of the driven grip tube for engaging the cam follower.

These and other aspects of the present invention will become apparent to those skilled in the art after a reading of the following description of the preferred embodiment when considered with the drawings.

BRIEF DESCRIPTION OF THE DRAWINGS

FIG. 2 is a sectional side view of the tattoo machine shown in FIG. 1, illustrating the interior of the housings and the removable grip tube including the needle bar; and FIG. 3 is a sectional top view of the removable grip tube of the present invention.

DESCRIPTION OF THE PREFERRED EMBODIMENTS

Figure 1:
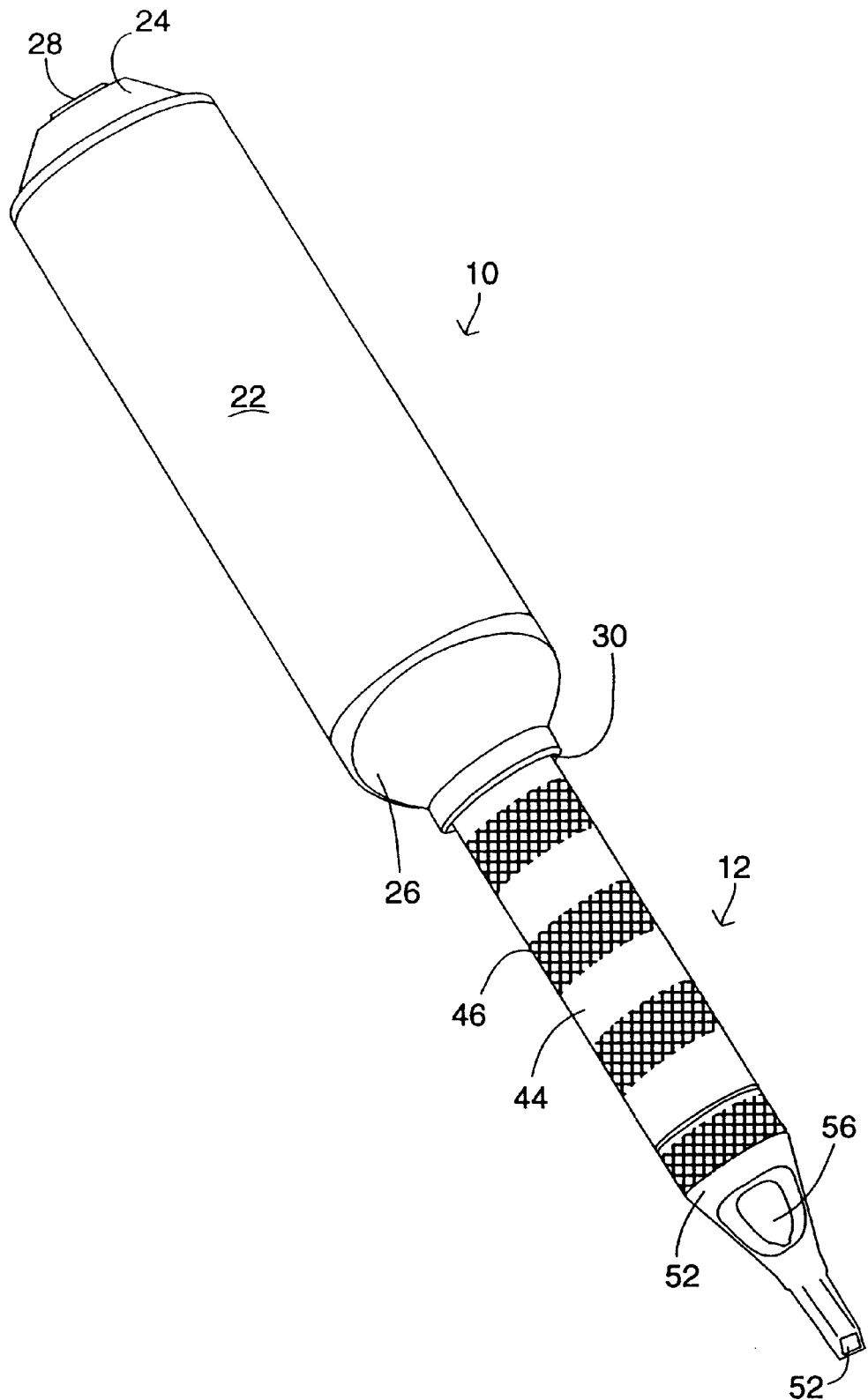
FIG. 1 is a perspective view of a tattoo machine constructed according to the present invention.

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIG. 1, a tattoo machine, generally designated 8, is shown constructed according to the present invention. The tattoo machine 8 includes two major subassemblies: a drive unit, generally 10, and a replaceable driven grip tube, generally 12.

Drive unit 10 includes an electric motor 14 having a drive shaft 16. A cam 18 having an angular cam face 20 is secured to the end of shaft 16. The internal components of drive unit 10 are enclosed by a housing formed of a cylindrical tubular section 22 with an end cap 24 at its proximal end and an adapter cap 26 at its distal end. End cap 24, which is removable for access to the interior of drive unit 10, is fitted with an electrical connector 28 to connect motor 14 to a source of electricity. Adapter cap 26 includes driven grip tube receiving bore 30 to receive drive unit 12. The axes of drive shaft 16 and receiving bore 28 are parallel to each other, and spaced so that the axis of receiving bore 28 intersects cam face 20 between its center and edge.

Driven grip tube 12 includes a needle bar 32 having a spherical cam follower 34 press fitted into its proximal end, and a flattened needle attachment plate or connector 36 at its distal end. A spring 38 is positioned around needle bar 32, and held in place by a flange 40 on needle bar 32 and a retainer 42 between spring 38 and needle connector 36.

The needle bar 32 is positioned within the bore of a cylindrical grip section 44, that has a plurality of circumferential knurled areas 46 to improve the operator's grip. The distal end of grip section 44 has a cross-section corresponding to the cross-section of receiving bore 30. A snug fit between bore 30 and grip section 44 is achieved with O-rings 48 and 50, reducing vibration and preventing fluid penetration.

The distal end of grip section 44 is joined to a tip section 52 that includes a bore axially aligned with the needle bar receiving bore of grip section 44. The bore of tip section 52 terminates in a needle exit opening 54 that is of a smaller diameter than the needle bar bore. Tip section 52 also includes a pigment reservoir 56 for introducing pigment into the interior of tip section 52 and into contact with a needle (not shown) attached to needle attachment surface 36. O-rings 58 and 60 provide a tight fit between tip section 52 and grip section 44.

The needle connector may be of different configurations, depending upon the type of needle used, and the manner of attachment. When a flat plate connector such as connector 36 is used, a means for preventing rotation of the needle bar may be needed to hold the connector in the desired position. For example, a flattened area 60 on the needle bar may engage a flattened area 62 on the interior of grip section 44 to prevent rotation.

In use, a needle is attached, e.g., by soldering, to needle connector 36. Needle bar 32 is then inserted into grip section 44 so that cam follower 34 protrudes from proximal end of the bore of section 44. Tip section 52 is then press fitted onto the distal end of section 44, so that a needle carried by connector 36 extends through the bore of tip section 52. Liquid pigment is introduced into pigment reservoir 56, and the tattoo machine is started by a foot switch (not shown) connected to the electrical power supply.

Rotation of drive shaft 16 and cam 18 causes cam follower 34 to ride along cam face 20. As the portion of cam face 20 closest to the distal end of the tattoo machine approaches cam follower 34, needle connector 36 is pushed toward the distal end of the tattoo machine, pushing the tip of the needle out of opening 54. Upon further rotation, spring 38 forces needle connector 36 back towards the proximal end of the tattoo machine.

Since cam follower 34 is in continuous contact with cam face 20, smooth and rapid reciprocation with minimal vibration is obtained. Also, due to the eccentric offset of the axes of the drive unit and driven grip tube, and the resultant configuration of the overall machine, the operator is able to hold grip section 44, which has a diameter of approximately 0.5 inch, much like a writing instrument. The relatively bulky drive unit 10, however, is positioned above the operator's hand so that it does not interfere with use of the tattoo machine.

During the application of a tattoo, the operator will frequently need to change from one color of pigment to another color. With the present invention, the operator simply removes a first driven grip tube 12 from drive unit 10 and inserts another previously prepared driven grip tube 12 for use with the next colored pigment. Thus, changing from one color, or needle, to another is fast and trouble free. In addition, the isolation of driven grip tube 10 from drive unit 12 due to its construction and the use of pairs of O-rings 48, 50 and 56, 58, minimizes the transmission of fluids into the drive unit, facilitating cleaning.

In addition, since spring 38 biases the needle bar 32 towards the cam face, a needle attached to the needle bar 32 retracts into 52 when driven grip tube 10 is removed from drive unit 12. This provides an extra degree of safety to the operator while protecting the needle from damage if the grip tube is accidentally dropped.

Certain modifications and improvements will occur to those skilled in the art upon a reading of the foregoing description. By way of example, cam follower 34 could be molded as one piece of the needle bar. Also, the driven grip tube could be formed in one piece of disposable plastic which is desirable for medical and cosmetic applications, such as permanent eye lining. It should be understood that all such modifications and improvements have been deleted herein for the sake of conciseness and readability but are properly within the scope of the following claims.

We claim:

1. A handheld tattoo machine, said apparatus comprising:
   (a) a driven grip tube, said driven grip tube having a first longitudinal axis and including a reciprocal needle bar;
   (b) a drive housing for receiving and driving said driven grip tube, said drive housing having a second longitudinal axis parallel to and offset from the first longitudinal axis of said driven grip tube to facilitate ease of operation of said tattoo machine, and further having a drive unit, said drive unit including a rotatable drive shaft having a third longitudinal axis also parallel to and offset from the first longitudinal axis of said driven grip tube, and a cam rotatable by said rotatable drive shaft, said cam having a cam face at an acute angle to said third longitudinal axis of said rotatable drive shaft; and
   (c) a spring adapted to urge said reciprocal needle bar toward said cam face.

2. The apparatus according to claim 1, wherein said reciprocal needle bar includes a cam follower at one end and a needle attachment surface at an opposed end.

3. The apparatus according to claim 2, wherein said drive unit further includes an electric motor.

4. The apparatus according to claim 3, wherein said rotatable shaft forms a part of said motor.

5. The apparatus according to claim 3, wherein said electric motor is adapted to receive a detachable power cord connected to a remote electrical power supply.

6. The apparatus according to claim 2, wherein said rotating shaft of said drive unit rotates between about 9000 to 10000 rpms under noload conditions.

7. The apparatus according to claim 2, wherein said rotating shaft of said drive unit rotates between about 3000 to 4000 rpms under load.

8. The apparatus according to claim 1, wherein said drive housing includes a driven grip tube receiving bore having a longitudinal axis parallel to and offset from the longitudinal axis of said drive housing.

9. The apparatus according to claim 8, wherein said driven grip tube includes at least one O-ring to frictionally secure said driven grip tube within said driven grip tube receiving bore.

10. A driven grip tube for a needle bar for attachment to a drive unit of a tattoo machine, said drive unit including a rotatable shaft with a first longitudinal axis, a cam rotatable by said shaft, said cam having a cam face at an acute angle to the first longitudinal axis of said rotatable shaft, and a driven grip tube receiving bore, said driven grip tube comprising:
    (a) an elongated cylindrical housing;
    (b) a longitudinally reciprocal needle bar received within said housing having a cam follower at one end for engagement with said cam face and a needle attachment surface at an opposed end; and
    (c) a spring adapted to urge said needle bar toward said cam face.

11. The apparatus according to claim 10, wherein said cam follower is a rotatable ball bearing fitted into the end of said needle bar.

12. The apparatus according to claim 10, wherein said needle attachment surface is a flat plate.

13. The apparatus according to claim 10, wherein said elongated housing includes a removable tip for retaining said needle bar within said housing.

14. A handheld tattoo machine, said apparatus comprising:
    (a) a driven grip tube including: (i) an elongated cylindrical housing; and (ii) a longitudinally reciprocal needle bar received within said housing having a cam follower at one end and a needle attachment surface at an opposed end;
    (b) a drive housing for receiving and driving said driven grip tube, said drive housing having a longitudinal axis parallel to and offset from the longitudinal axis of said grip tube to facilitate ease of operation of said tattoo machine, wherein said drive housing further includes a drive unit including a rotatable drive shaft and a cam attached to the distal end of said shaft, said cam having a cam face at an angle to the longitudinal axis of said driven grip tube for engaging said cam follower; and
    (c) a spring adapted to urge said needle bar toward said cam face.

15. The apparatus according to claim 14, wherein said drive unit further includes an electric motor.

16. The apparatus according to claim 15, wherein said rotatable shaft forms a part of said motor.

17. The apparatus according to claim 15, wherein said electric motor is adapted to receive a detachable power cord connected to a remote electrical power supply.

18. The apparatus according to claim 14, wherein said rotating shaft of said drive unit rotates between about 9000 to 10000 rpms under noload conditions.

19. The apparatus according to claim 14, wherein said rotating shaft of said drive unit rotates between about 3000 to 4000 rpms under load.

20. The apparatus according to claim 14, wherein said drive housing includes a driven grip tube receiving bore having a longitudinal axis parallel to and offset from the longitudinal axis of said drive housing.

21. The apparatus according to claim 20, wherein said driven grip tube includes at least one O-ring to frictionally secure said driven grip tube within said driven grip tube receiving bore.

22. The apparatus according to claim 14, wherein said cam follower is a rotatable ball bearing fitted into the end of said needle bar.

23. The apparatus according to claim 14, wherein said needle attachment surface is a flat plate.

24. The apparatus according to claim 14, wherein said elongated housing includes a removable tip for retaining said needle bar within said housing.

* * * * *